United States Patent
Isolauri et al.

(10) Patent No.: US 7,112,322 B2
(45) Date of Patent: Sep. 26, 2006

(54) PROBIOTICS IN PRIMARY PREVENTION OF ATOPIC DISEASES

(76) Inventors: Erika Isolauri, Tallmonkuja 6, FIN-21120, Raisio (FI); Seppo Salminen, Puutarhakatu 2 C 32, FIN-20100, Turku (FI)

( * ) Notice: Subject to any disclaimer, the term of this patent is extended or adjusted under 35 U.S.C. 154(b) by 139 days.

(21) Appl. No.: 10/311,706

(22) PCT Filed: Jun. 20, 2001

(86) PCT No.: PCT/FI01/00588

§ 371 (c)(1),
(2), (4) Date: Dec. 19, 2002

(87) PCT Pub. No.: WO01/37865

PCT Pub. Date: May 31, 2001

(65) Prior Publication Data

US 2003/0180272 A1 Sep. 25, 2003

(30) Foreign Application Priority Data

Jun. 20, 2000 (FI) ................................. 20001460

(51) Int. Cl.
- *A23C 9/12* (2006.01)
- *A01N 63/00* (2006.01)
- *C12N 1/00* (2006.01)
- *C12N 1/20* (2006.01)

(52) U.S. Cl. ...................... 424/93.45; 426/34; 426/61; 435/252.9; 435/856

(58) Field of Classification Search ............. 435/252.1, 435/7.1, 326, 971, 252.9, 856; 424/93.1, 424/130.1, 136.1, 278.1, 93.45; 426/34, 426/61

See application file for complete search history.

(56) References Cited

FOREIGN PATENT DOCUMENTS

| | | |
|---|---|---|
| JP | 2000-086524 A | 3/2000 |
| WO | WO 96/36880 A1 | 11/1996 |
| WO | WO 97/00078 A1 | 1/1997 |
| WO | WO 99/53777 A1 | 10/1999 |
| WO | WO 01/37865 A1 | 5/2001 |

OTHER PUBLICATIONS

Uhlemann, Marlies, et al. Z. Geburtsh. Neonatol., vol. 203, pp. 213-217, 1999.
Kirjavainen, P.V. et al. Allergy, vol. 54, No. 9., pp. 909-915, 1999.
Sudo, Nobuyuki, et al. Journal of Immunology. vol. 159, No. 4, pp. 1739-1745, 1997.
Majamaa, Heli, et al. J. Allergy Clin. Immunol, vol. 99, No. 2, pp. 179-185, 1997.
Bjorksten, B., et al. Clinical and Experimental Allergy. vol. 29, No. 3, pp. 342-346, 1999.
E. Isolauri et al., Journal of Pediatrics, vol. 120, No. 1, pp. 9-15, Jan. 1992.
E. Isolauri et al., Clinical and Experimental Allergy, vol. 30, pp. 1604-1610, 2000.
E. Isolauri et al., Gastroenterology, vol. 105, pp. 1643-1650, 1993.
M. Kailiomaki et al., J. Clin. Immunol., vol. 104, No. 6, pp. 1251-1257, 1999.
H. Majamaa, et al., J. Allergy Clin. Immunol., vol. 97, No. 4, pp. 985-990, 1996.
T. Pessi, J. Nutr., vol. 128, pp. 2313-2318 (1998).

*Primary Examiner*—David M. Naff
*Assistant Examiner*—Deborah K. Ware
(74) *Attorney, Agent, or Firm*—Birch, Stewart, Kolasch & Birch, LLP

(57) ABSTRACT

The present invention is in the field of prophylaxis of allergies, and relates specifically to primary prevention of atopic diseases by administering probiotic bacteria, beneficial microbes of the healthy gut flora, pre- and postnatally to children at high risk of atopic diseases. In an embodiment, probiotic bacteria are administered to a pregnant woman at least two weeks before infant delivery and after delivery, probiotic bacteria are administered to the newborn infant for at least two months. The amount of probiotic bacteria administered is about $1\times10^8$ to about $1\times10^{10}$ colony forming units of the probiotic bacteria.

2 Claims, 3 Drawing Sheets

PROBIOTICS IN PRIMARY PREVENTION OF ATOPIC DISEASES

This application is the national phase under 35 U.S.C. § 371 of PCT International Application No. PCT/FI01/00588 which has an International filing date of Jun. 20, 2001, which designated the United States of America.

FIELD OF THE INVENTION

The present invention is in the field of prophylaxis of allergies, and relates specifically to primary prevention of atopic diseases by administering probiotic bacteria, beneficial microbes of the healthy gut flora, pre- and postnatally to children at high risk of atopic diseases.

BACKGROUND OF THE INVENTION

At present allergy, manifested as atopic diseases—atopic eczema, allergic rhinitis and asthma—represents a chronic disorder of rising importance in economically developed countries world-wide. The demonstration of an inverse association between infections early in life and atopy represents a substantial advance which has led to renewed scientific interest in the hygiene hypothesis introduced a decade ago, according to which the recent rapid increase in atopy may in fact be due to improved hygiene and reduced family size. Recent epidemiological studies have yielded results both for and against this hypothesis.

Gastrointestinal microflora promote processes with a potential to counter allergy: 1) T helper 1-type immunity, 2) generation of transforming growth factor-$\beta$ (TGF-$\beta$), which has a vital role both in the suppression of Th2-induced allergic inflammation and in induction of oral tolerance and 3) IgA production, an indispensable component in the mucosal immune defence (Sanfilippo et al., 2000; Isolauri et al., 2000). The gut microflora may thus represent a major postnatal counter-regulator of the universal Th2-skewed immune system of pregnancy and neonatal age. Confrontation with microbial antigens in the gastrointestinal tract begins instantly after birth, and the viable cells of a fully established gut microflora outnumber those of the host by a factor of ten. Consequently, commensal gastrointestinal microbes constitute the earliest and most substantial stimulus for the development of gut-associated lymphoid tissue.

Probiotics, defined as live microbial food ingredients beneficial to health, are normal commensal bacteria of the healthy human gut microflora. The most frequently used genera are lactobacilli and bifidobacteria. Probiotics are known to reverse the increased intestinal permeability characteristic of children with atopic eczema and food allergy, and to enhance gut-specific IgA responses, frequently defective in children with food allergy (Isolauri et al, 1993; Majamaa and Isolauri, 1996; Isolauri, 1992). Promotion of gut barrier function by means of probiotics also includes normalization of the gut microecology, alterations in which have been demonstrated in allergic subjects. Recent studies indicate that certain probiotics alleviate changes related to allergic inflammation both in vitro and in vivo (Isolauri et al., 2000; Majamaa and Isolauri, 1997). A probiotic strain, *Lactobacillus casei*, ssp. *rhamnosus* (*Lactobacillus* GG; ATCC 53103), has been proven safe at an early age and effective in the treatment of allergic inflammation and food allergy. Specific strains in the gut indigenous microflora thus exert profound effects on the physiology and immunology of the host.

At birth the human gastrointestinal tract is sterile, but during the first months and years of life a rapid sequential colonization occurs, leading to stable indigenous gut microflora. Simultaneously, the universally Th2-dominant immunity of newborns is intensified in atopic individuals, with the subsequent expression of atopic disease. In addition to normal microflora impacting on the neonatal gastrointestinal system, another massive and constant antigen source is confronted in the form of dietary antigens. Recent animal studies indicate that these may potentiate atopic-type immunity at both mucosal and systemic level. Any process designed to counter-regulate allergy must thus exert its major effects in infancy, and preferably during the initial encounters with dietary antigens. Here probiotics are eminently appropriate for the task, not only as regards timing but also in their capacity to reduce the dietary antigen load by degrading and modifying macromolecules (Pessi et al., 1998).

SUMMARY OF THE INVENTION

In the present application we clinically demonstrate that specific probiotics substantially reduce the prevalence of atopic eczema, which indicates that such microbes prevent atopic disease. On the other hand, further data obtained in our gut colonisation studies with bifidobacteria, presented in this application, demonstrate that differences in gut microflora precede the development of atopy. Based on the data we propose that exposure to specific strains of commensal microflora represents a key protective modular of immunity against atopy and subsequent atopic diseases and, consequently, that probiotics promoting early bifidogenic gut microflora have a preventive potential in allergy.

DETAILED DESCRIPTION OF THE INVENTION

Figure 1:
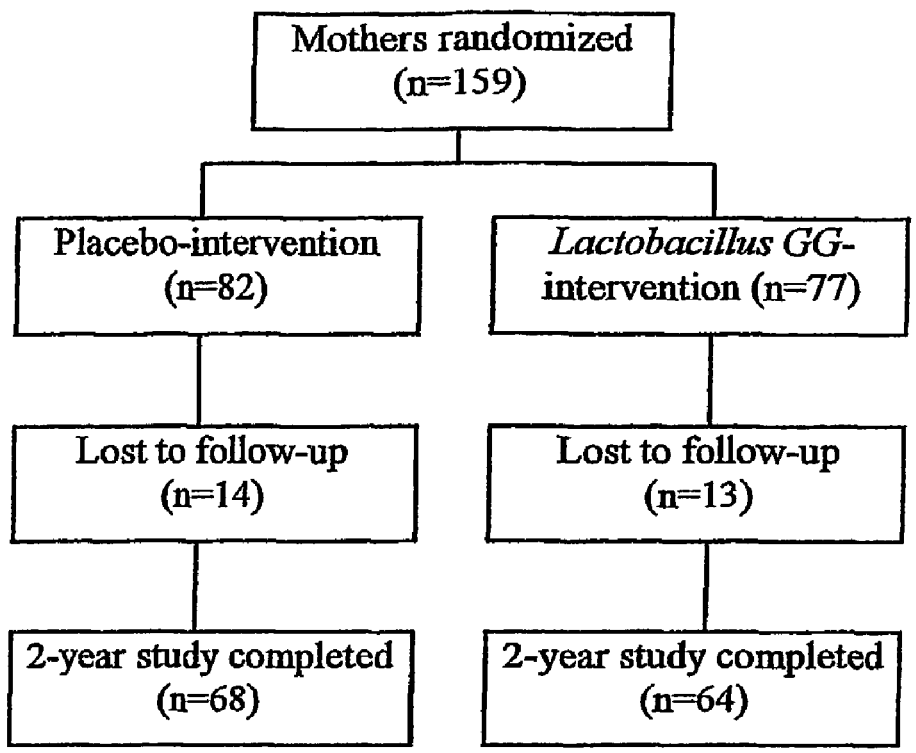
FIG. 1 shows the profile of the *Lactobacillus* GG trial.

The present invention provides a method for primary prevention of atopic diseases in an infant at high risk of such diseases, in which method to a pregnant woman a daily dose of live probiotic bacteria is administered for at least two weeks before delivery and, after delivery, a daily dose of live probiotic bacteria is administered to the newborn infant for at least 2 months.

After delivery, the probiotic bacteria can be administered via the breastfeeding mother, or directly to the newborn infant. Any daily dose of the bacteria giving a desired effect can be used, a suitable dose is about $1 \times 10^8$ to about $1 \times 10^{10}$ colony forming units of probiotic bacteria.

Consequently, the invention also relates to the use of probiotic bacteria for the preparation of a composition useful for primary prevention of atopic diseases in an infant at high risk of atopic diseases, to be administered according to the pattern as indicated above.

Probiotic bacteria which can be used in this invention are for instance lactic acid bacteria or bifidobacteria. A suitable lactic acid bacterial strain is *Lactobacillus casei* ssp. *rhamnosus* (ATCC 53103), and an appropriate bifidobacterial strain is *Bifidobacterium lactis* Bb-12. Also other bacterial strains can be used, to which probiotic characteristics have been shown.

Further, a mixture of lactic acid bacteria and bifidobacteria can be administered.

Preferred probiotics for the purposes of this invention are probiotic bacteria which have the characteristics of promoting early bifidogenic gut microflora. Such probiotics strengthen the integrity of the gut and increase the proportion of bifidobacteria in gut microflora.

By administering probiotic bacteria according to the present invention to an infant at high risk, in order to primarily prevent atopic disease, the intestinal flora of the infant is affected propitiously. While starting the treatment during the mother's pregnancy, the amount of protective factors, such as antiinflammatory cytokines, of breast milk will be increased. By prevention of an allergic inflammatory state in this way, it is possible to prevent the breaking out of an atopic disease.

The expression "primary prevention" used in the present application means a prophylactic treatment for the purpose of totally preventing the breaking out of a disease in a subject at risk. On the other hand, the expression "secondary prevention" used in the art is understood to include means for preventing or alleviating the symptoms of an allergic disease already broken out or developed, e.g. preventing food allergy by eliminating the allergising food ingredients from the diet.

The present study is the first prospective clinical demonstration of a specific microbe preventing atopic disease, and the new insight may provide an excellent opportunity to devise strategies against allergy.

In the present study *Lactobacillus* GG (ATCC 53103) was introduced prenatally via mothers and postnatally for 6 months to infants at high risk of atopic diseases in a double-blind, randomized placebo-controlled trial of prevention of atopic disease.

One inclusion criterion for the study was a family history of atopic disease, i.e. one or more family members (mother, father and/or older sibling) with atopic eczema, allergic rhinitis or asthma. Families were recruited in antenatal clinics in the City of Turku (population 170 000) between February 1997 and January 1998, during a year, to avoid the effect of birth month on atopic sensitization. Altogether 159 mothers were randomized by means of a computer to receive two capsules of placebo (microcrystalline cellulose) or $1 \times 10^{10}$ colony-forming units of *Lactobacillus* GG (Valio Ltd, Finland) once a day for 2 to 4 weeks before delivery. After delivery breastfeeding mothers had the option of consuming capsules themselves, or otherwise the agents were introduced into the diets of the infants. In the latter case, the contents of the capsule were administered by spoon after mixing in water. Both of these modes of administration, via mother or to infant, have been shown to result in comparable amounts of *Lactobacillus* GG in infant feces (Majamaa and Isolauri, 1997). *Lactobacillus* GG and placebo capsules and their contents looked, smelled and tasted identical. Capsules were consumed for 6 months postnatally. Codes were kept by the supplier until all data were collected and analyzed.

The study was approved by the Committees on Ethical Practice in Turku University Hospital and the Health Office of the City of Turku. Written informed consent was obtained from the children's parents.

The children were clinically and immunologically examined during the neonatal period and on subsequent study visits at the ages of 3, 6, 12, 18 and 24 months of life. A physical examination, always undertaken by the same physician, included inspection of eyes, ears, nose and skin, auscultation of heart and lungs, palpation of abdomen, and evaluation of growth and neurological development. Parents were asked about their infant's signs and symptoms possibly related to atopic diseases (skin: redness, dryness, oozing, scratching (itch); eyes and nose: redness, discharge, sneezing, rubbing (itch); lungs: cough, wheeze, shortness of breath). The assays for serum total IgE and specific IgE antibodies to milk, egg, cat and house dust mite were carried out with Pharmacia CAP FEIA immunoassay on UniCAP 100 automatic analyzer (Pharmacia & Upjohn, Uppsala, Sweden) according to manufacturer's instructions. An antigen-specific IgE value of more than 0.35 kU/l was considered increased. Skin prick test reactions were read at 10 minutes, and half of the histamine dihydrochloride (10 mg/ml; ALK Abelló, Horsholm, Denmark; ALK) reaction size (2+) or more was recorded as positive on the condition that the mean diameter of the wheal was at least 3 mm and the negative control (ALK) at the same time was 0 mm. Antigens tested included milk containing 1.5% fat, wheat flour diluted 1:10 (w/v) with 0.9% (w/v) sodium chloride, rye flour diluted 1:10 (w/v) with 0.9% (w/v) sodium chloride, gliadin diluted 1:1000 (w/v) with 0.9% (w/v) sodium chloride, egg white (ALK), cod (ALK), soya bean (ALK), latex (Stallergens, France), birch (ALK), six local grasses (all from ALK), cat (ALK), dog (ALK) and *Dermatophagoides pteronyssimus* allergen Der p1 (ALK). In addition, banana, potato and carrot were tested by prick-prick technique. Skin prick results were considered positive if an infant manifested at least one positive reaction to the antigens tested.

Chronic recurring atopic eczema at the age of two years was considered the primary endpoint, since it represents the principal manifestation of atopic diseases during the first years of life. The subjects were grouped as suffering from this disorder (children with atopic eczema) or not (healthy children). Atopic eczema was confirmed if the following features were detected: pruritus, facial and/or extensor involvement, and chronic relapsing course. The last-mentioned criterion was fulfilled if there was manifest eczema with a duration of one month or longer at the 24 month study visit and on at least one previous visit. The fourth major criterion, a family history of atopic disease, was one inclusion criterion for the study. The diagnosis of allergic rhinitis was established if two or more subsequent symptoms were experienced on most days: nasal discharge, blockage, sneezing, and itching. A temporal relationship of these symptoms with allergen exposure, relief of symptoms upon antihistamine treatment and evidence of atopic sensitization (i.e. positive skin prick test and/or positive radioallergosorbent assay) were sine qua non. The diagnosis of asthma was based on an algorithm created by an international pediatric asthma consensus group. Asthma was diagnosed if an infant had chronic or recurrent cough, wheeze and/or shortness of breath suggestive of asthma, and if alternative diagnoses were excluded, and if trial antiasthma treatment was effective.

The base-line characteristics of the study subjects were similar in the placebo and *Lactobacillus* GG groups (Table 1). A total of 132/159 (83%) subjects completed the 2-year study. With at least 56 subjects in both groups an absolute risk reduction of 25% (50% risk in the placebo group and 25% in the *Lactobacillus* GG group) in the prevalence of atopic disease could be detected at a 5% level of significance with 80% power. The respective discontinuation rates were comparable (FIG. 1).

Figure 2:
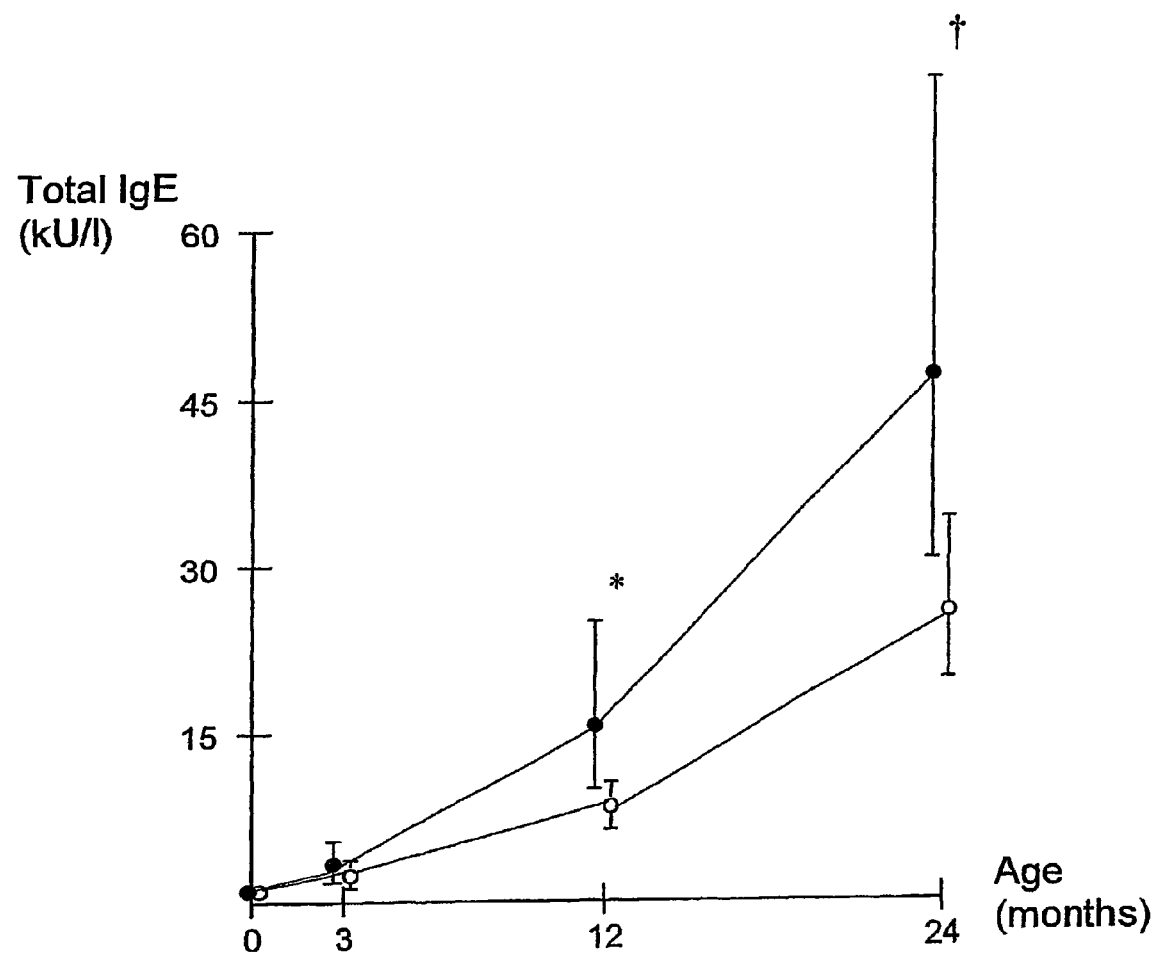
FIG. 2 shows the geometric mean concentrations of total IgE antibodies during the first two years of life in healthy children (open circle) and children with atopic eczema at the age of two years (closed circle). Error bar represents 95% confidence interval. *p=0.009 and †p=0.02, children with atopic eczema vs. healthy children (unpaired t-test).

Atopic eczema was diagnosed in 46/132 (35%) children at the age of two years. Five of these children also fulfilled the diagnostic criteria for asthma and one for both asthma and allergic rhinitis. The duration of breastfeeding was comparable between infants manifesting atopic eczema, 7.0 (5.8 to 8.2) months, and those without 6.7 (5.9 to 7.5) months; mean (95% CI) (p=0.65 by unpaired t-test). The age at the onset of symptoms of atopic eczema was 4.9 (3.9 to 6.2) months; geometric mean (95% CI). The objective SCORAD at the age of 24 months was 10 (9 to 11) in children with atopic eczema; geometric mean (95% CI). In children with atopic eczema the progressive IgE concentrations became manifested by the age of two years (FIG. 2). Skin prick test reactivity to common environmental antigens was more common in children with atopic eczema than in healthy children at the ages of 12 and 24 months (p=0.03 and p=0.01, respectively by $\chi^2$ test) while the frequency of increased antigen-specific IgE concentrations in serum was comparable between the groups (p=0.22 and 0.31, respectively by $\chi^2$ test). The most common antigens eliciting positive reactions by either method were egg and cow milk.

The prevalence of atopic eczema was reduced to half in infants given the probiotic, 15/64 (23%), as compared with that in those receiving placebo, 31/68 (46%) (p=0.008 by $\chi^2$ test). The number needed to treat with 95% CI was 4.5 (2.6 to 15.6).

Most mothers, 28/43 (65%), in the probiotic group breastfeeding for at least 6 months chose the option of consuming the probiotic capsules themselves. The preventive effect did not depend on the mode of administration, since in the *Lactobacillus* GG-intervention group atopic eczema was diagnosed in 9/36 (25%) cases if the infants consumed the pro-biotic themselves and in 6/28 (21%) cases if the strain was consumed by the breastfeeding mothers (p=0.74 by $\chi^2$ test). The preventive effect of *Lactobacillus* GG was most marked in children already evincing IgE antibodies in cord blood; 3/20 (15%) infants with detectable IgE in cord blood receiving *Lactobacillus* GG developed atopic eczema as compared with 9/19 (47%) receiving placebo; relative risk 0.32 (0.10 to 0.99) (p=0.03 by $\chi^2$ test). The concentration of total IgE and the frequencies of increased antigen-specific IgE concentrations and of positive reactions in skin prick tests were comparable between infants who consumed the probiotic and those receiving the placebo (Table 2). The frequency of cases with high total IgE concentration (>93.3 kU/l) tended to be lower in the probiotic, 11/61 (18%), than in the placebo group, 17/63 (27%), at two years; relative risk (95% CI) 0.67 (0.34 to 1.29). The total IgE concentration was rated high, if greater than the geometric mean concentration of total IgE+ one standard deviation in children without atopic disease.

TABLE 1

Comparison of base-line characteristics of the study subjects

| | Placebo group (n = 82) | Lactobacillus GG group (n = 77) |
|---|---|---|
| Family history: | | |
| Maternal atopic disease | 63/82 (77%) | 55/77 (71%) |
| Older sibling | 30/82 (37%) | 26/37 (34%) |
| Parent(s) smoking | 17/82 (21%) | 9/77 (12%) |
| Furry pet at home | 9/82 (11%) | 16/77 (21%) |
| Birth characteristics: | | |
| Weeks of gestation[a] | 39.4 (39.0 to 39.7) | 39.4 (39.0 to 39.7) |
| Male gender | 43/82 (52%) | 49/77 (64%) |
| Cord blood IgE (kU/l)[b] | 0.04 (0.02 to 0.06) | 0.06 (0.03 to 0.12) |
| Head circumference (cm)[a] | 35.0 (34.7 to 35.3) | 35.2 (34.8 to 35.5) |
| Weight (g)[a] | 3610 (3510 to 3720) | 3630 (3520 to 3740) |

Values are numbers (percentages) of cases of maternal atopic disease, older sibling, parent/s who smoke/s and furry pet at home
[a] Value represents mean (95% confidence interval)
[b] Value represents geometric mean (95% confidence interval)

TABLE 2

Atopic sensitization in the intervention groups

| | Placebo group (n = 68) | Lactobacillus GG group (n = 64) | p-value |
|---|---|---|---|
| Total IgE (kU/l)[a]: | | | |
| 3 months | 3.0 (2.4 to 3.7) | 3.1 (2.5 to 4.0) | 0.79[d] |
| 12 months | 9.7 (7.0 to 13.4) | 11.2 (8.0 to 15.7) | 0.55[d] |
| 24 months | 32.7 (22.6 to 47.3) | 31.3 (22.8 to 43.0) | 0.85[d] |
| Increased RAST readings[b]: | | | |
| 3 months | 2/66 (3%) | 2/58 (3%) | 0.90[e] |
| 12 months | 15/66 (23%) | 16/62 (26%) | 0.68[e] |
| 24 months | 16/64 (25%) | 17/62 (27%) | 0.76[e] |
| Prick test reactivity[c]: | | | |
| 6 months | 7/68 (10%) | 11/64 (17%) | 0.25[e] |
| 12 months | 12/68 (18%) | 17/63 (27%) | 0.20[e] |
| 24 months | 9/65 (14%) | 11/61 (18%) | 0.52[e] |

[a] Value represents the geometric mean (95% confidence interval)
Value represents the numbers (percentages) of infants evincing at least
[b] one increased (>0.35 kU/l) antigen-specific IgE concentration in radio-allergosorbent (RAST) assay or
[c] one positive reaction in skin prick testing.
[d] Unpaired t-test and
[e] X2 test (placebo vs. Lactobacillus GG)

The Gut Colonisation Studies

In the studies with bifidobacteria we prospectively followed 76 high-risk infants from birth to the age of one year, when the development of atopic sensitisation was determined by skin prick testing. Since the major and primary microbial stimulation occurs along with the establishment of the gut microflora, we hypothesised that exposures to commensal microflora outnumber sporadic infections and that this may be related to other changes predisposing to atopy, thus representing a key modulator of the immune system in the newborn.

Research on the gastrointestinal microflora by conventional bacterial culture has been hampered by the lack of sensitivity in methods of assessment, as almost half of the bacteria in the gut are unculturable, if nonetheless viable. We therefore utilised, in addition to bacterial cultivation, two culture-independent methods: gas-liquid chromatography (GLC) of bacterial cellular fatty acids and quantitative fluorescence in situ hybridisation (FISH) of bacterial cells to characterise the gut microflora during the first months of life in infants later developing or not developing atopy.

Subjects and Study Design

The study cohort comprised 76 volunteer families with 76 newborn infants, randomly selected from the population of an allergy-prevention study evaluating the preventive potential of probiotics in atopy. In this study population 30/76 (39%) infants had one and 46/76 (61%) several first-degree close relatives with atopic eczema, allergic rhinitis or asthma.

The study was approved by the Committees on Ethical Practice in Turku University Central Hospital and the Health Office of the City of Turku. Written informed consent was obtained from the children's parents.

The infants were born between the $36^{th}$ and $42^{nd}$ weeks of gestation (mean 40). They were clinically examined at the ages of 2 days, 3 weeks, and 3, 6 and 12 months. Any signs and symptoms of atopic disease were recorded. Atopic sensitisation at the age of 12 months, evaluated by skin prick testing, was considered a primary endpoint. Infants were considered atopics if they evinced at least one positive reaction to the antigens tested, whereas those without positive reaction were considered non-atopics. Double-blind placebo-controlled cow milk challenge was applied when symptoms, clinical signs or skin prick tests were suggestive of cow milk allergy.

Diagnosis of Atopic Dermatitis

The diagnosis of atopic dermatitis was based on criteria previously described (Hanifin, 1991). Briefly, atopic dermatitis was confirmed if the following three major features were detected: pruritus, typical morphology and distribution, and chronic dermatitis (duration of one month or longer).

Evaluation of Atopic Sensitisation

Atopic sensitisation was evaluated by skin prick testing as previously described (Majamaa and Isolauri, 1997). Reactions were read at 10 minutes, and half of the histamine dihydrochloride (10 mg/ml; ALK Abelló, Horsholm, Denmark; ALK) reaction size (2+) or more was recorded as positive on the condition that the mean diameter of the wheal was at least 3 mm, and the negative control (ALK) at the same time was 0 mm. Antigens tested included milk containing 1.5% fat, wheat flour diluted 1:10 (w/v) with 0.9% (w/v) sodium chloride, rye flour diluted 1:10 (w/v) with 0.9% (w/v) sodium chloride, gliadin diluted 1:1000 (w/v) with 0.9% (w/v) sodium chloride, egg white (ALK), cod (ALK), soybean (ALK), latex (Stallergens, France), birch (ALK), six local grasses (ALK), cat (ALK), dog (ALK) and *Dermatophagoides pteronyssimus* allergen Der p1 (ALK). In addition, banana, potato and carrot were tested by prick-prick technique.

Diagnosis of Cow Milk Allergy

The diagnosis of cow milk allergy was based on an unambiguous relationship between ingestion of cow milk and clinical symptoms, i.e. the symptoms disappeared after elimination of cow milk from the diet, and an unequivocal relapse occurred in a double-blind, placebo-controlled cow milk challenge. This challenge was carried out as described elsewhere (Kalliomäki et al, 1999).

Cultivation of Stool Samples

A faecal sample from the infant was taken either by nursing staff at scheduled visit or immediately prior to it by parents. In the latter case, the sample was stored at 4° C. and delivered to the hospital within 24 hours for immediate cultivation. A stool sample was obtained from 71 infants at the age of 20 days (18 to 21 days) and from 69 at the age of 14 weeks (13 to 14 weeks); mean (95% CI). The rest of the sample was immediately frozen and stored at −20° C. until analysed by GLC and FISH. No quantitative culture methods were employed. The bacteria were cultured on 6 different freshly prepared media, i.e. Blood Agar (Pronadisa, Madrid, Spain) for gram-negative rods; agar (Leiras, Turku, Finland) supplemented with Mycological Peptone (Oxoid, Basingstoke, United Kingdom) and glucose for yeasts and fungi; Bile Eskulin Azide Agar (Difco, Detroit, USA) for enterococci; Blood Agar (Pronadisa) supplemented with glucose, yeast extract (LAB M, Bury, United Kingdom), L-cysteine HCl (Merck, Darmstadt, Germany), metadion (Merck) and neomycin sulfate (Sigma, St. Louis, USA) for anaerobes; *Clostridium difficile* Agar (Oxoid) supplemented with hemin (Sigma), neutralred (Merck), D-Cycloserine (Sigma), egg and Cefoxitin (MSD, Haarlem, the Netherlands) for *Clostridium difficile*; and Rogosa SL agar (Difco) for *Lactobacillus*-like bacteria. The first three media were incubated aerobically and the last three anaerobically at 35° C. for 48 h. Subsequently, identification of different species was made according to their growth on selective media, colonies, color and cell morphology.

Gas-Liquid Chromatography of Bacterial Fatty Acids

The method has previously been described in detail (Eerola and Lehtonen, 1988). After separation of bacterial material from faecal vegetable fibres and free fatty acids, the sample was remixed and allowed to sediment for 15 min. Thereafter the bacterial component was isolated by centrifuging at 1000 g for 15 min at room temperature and removing the supernatant. The collected bacterial mass was saponified and methylated. The methylated fatty acids were then extracted with ethyl ether and hexane. GLC analysis was performed with an HP5890A gas chromatograph (Hewlett-Packard) and an Ultra 2004-11-09B fused silica capillary column (0.2 mm by 25 m; cross-linked 5% phenylmethyl silicone; Hewlett-Packard). A recently developed computerised bacterial identification program was used to analyse the GLC profiles of the faecal samples. The analysis was based on the correlation and cluster analysis of the fatty acid spectra of individual samples. All peaks of individual fatty acids in the chromatograms were used in comparisons.

Fluorescence In Situ Hybridization of Bacterial Cells

Faecal samples were suspended in 0.1M phosphate buffered saline (pH 7.0) to give a final concentration of 10% (w/v). The slurries were homogenized and centrifuged at low power (250 g for 2 min) to remove particulate matter. Bacterial cells were fixed and FISH performed as previously described (Langendijk et al., 1995). In brief, cells were fixed overnight in 4% (v/v) paraformaldehyde at 4° C., washed twice in PBS and stored at −20° C. in a PBS:ethanol (1:1) solution. Subsamples of the fixed cells were hybridised overnight in hybridisation buffer with 5 ng×μL$^{-1}$ Cy3 indocarbocyanin-labelled oligonucleotide probe. Probes included were Bac303 (CCAATGTGGGGGACCTT)(SEQ ID NO: 1) specific for bacteroides, Bif164 (CATCCGGCATTACCACCC)(SEQ ID NO: 2) for bifidobacteria, His150 (TTATGCGGTATTAATCT(C/T)CCTTT)(SEQ ID NO: 3) for clostridia and Lab158 (GGTATTAGCA(T/C)CTGTTTCCA)(SEQ ID NO: 4) for lactobacilli and enterococci; (sequence 5'→3'). Total cell numbers were counted using a nucleic acid stain 4',6-diamidino-2-phenylindole (DAPI). Cells were washed with the hybridisation buffer, filtered through a 0.2 μm polycarbonate filter (Millipore Corporation, Bedford, USA) and mounted on a slide with SlowFade® (Molecular Probes Inc., Eugene, USA). They were counted visually using a Leica Laborlux D epifluorescence microscope mounted with Cy3 and DAPI specific filters. Fifteen microscopic fields were counted per assay.

Statistics

Normally distributed data are expressed as means with 95% confidence interval (CI) and those of skewed distribution as geometric means with 95% CI after logarithmic (log) transformation. Unpaired t-test was applied to compare values between the groups. The $\chi^2$-test was used to compare proportions between the groups.

The entire analysis of the GLC data was based on paired comparisons between individual samples and calculation of similarity indices between them. Similarity indices were presented as correlation matrices and further analysed by weighted pair-group cluster analysis of arithmetic means. The faecal samples were divided into four different groups for analysis of the results of GLC of bacterial cellular fatty acids according to the atopic status of the infant (atopic vs. non-atopic) and sampling time (age 3 weeks vs. 3 months). Statistical significance between atopics and non-atopics at different time points was calculated by comparing the variation in fatty acid profiles within the groups to that between the groups. The within-group variation was determined by calculating the mean (SD) of the similarity indices of all paired comparisons within the group. That between two different groups was obtained by calculating the mean (SD) of all paired similarity indices between samples in both groups. Subsequently, the inter-group variation was compared with that within the groups by calculating a Z-value as previously described. The Z-value was used to determine the p-value by means of a Z-table. P<0.05 was considered statistically significant.

RESULTS

Atopic Sensitisation and Clinical Characteristics

At the age of 12 months atopic sensitisation was observed in 22/76 (29%) children. Skin prick test reactivity to egg, cow milk, wheat, cat and latex was seen in 19/22 (86%), 5/22 (23%), 3/22 (14%), 2/22 (9%) and 1/22 (5%) atopics, respectively. No skin prick reactivity to any other antigen tested was seen. Five atopics were polysensitised, i.e. they evinced positive skin prick test reactivity to at least two different antigens. Half of the atopics, 11/22 (50%), manifested atopic dermatitis and 9/22 (41%) were allergic to cow milk as diagnosed by double-blind placebo-controlled cow milk challenge.

A maternal atopic history was observed in 19/22 (86%) atopics and 45/54 (83%) non-atopics (p=0.74). Atopics and non-atopics were comparable for birth characteristics. The means of length, weight and head circumference at birth were 51.2 (50.3 to 52.8) cm, 3600 (3410 to 3790) g and 35.1 (34.5 to 35.7) cm, respectively, in atopics and 50.6 (50.1 to 51.1) cm, 3610 (3480 to 3740) g and 35.1 (34.7 to 35.5) cm, respectively, in non-atopics (p=0.24, p=0.94, p=0.98, respectively); mean (95% CI).

At the ages of 3 weeks and 3 months dietary characteristics were comparable between atopics and non-atopics (Table 3). At 3 months 9/54 (17%) non-atopics but none of the atopics had received antibiotics, p=0.04.

Neonatal Gastrointestinal Microflora

According to bacterial cultivation, there were no differences in neonatal gut microflora between infants developing and not developing atopy (Table 4). At the same time, however, there was a statistically significant difference between the groups in the bacterial cellular fatty acid profile of stool samples (FIG. 3) (p=0.005). In order to detect the bacteria possibly responsible for the discrepancy, FISH of faecal bacteria was applied to 29 samples; the results demonstrated that the ratio of bifidobacteria to clostridia was reduced in atopics, 19 (3 to 122), as compared to that in non-atopics, 185 (57 to 604); geometric mean (95% CI) (p=0.03). The difference was caused by a tendency towards lower counts of bifidobacteria and higher counts of clostridia in atopics (Table 5).

Gastrointestinal Microflora at the Age of 3 Months

Figure 3:
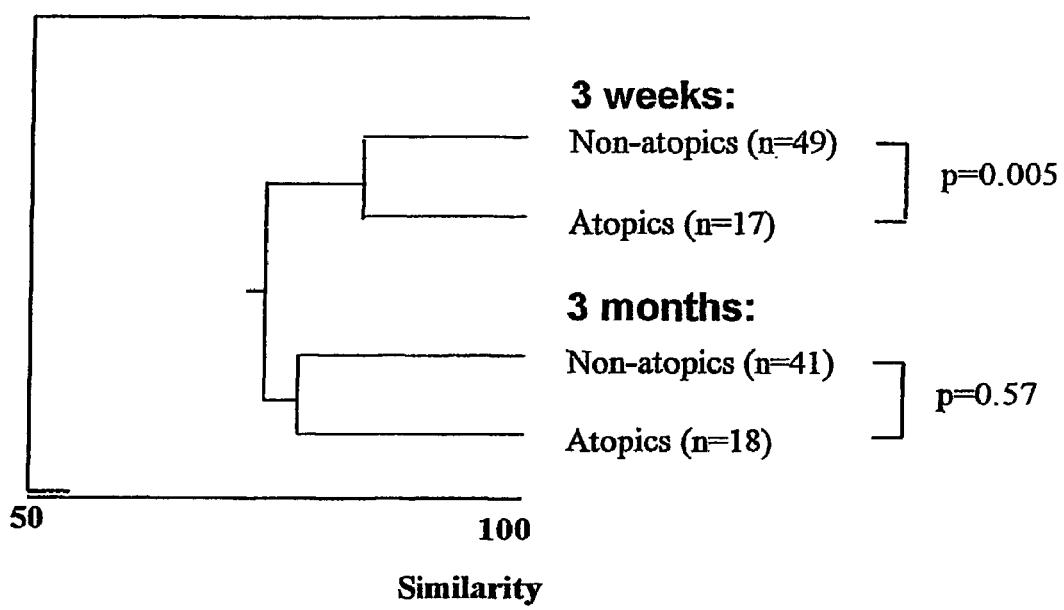
FIG. 3 shows a dendrogram representing relative similarities of bacterial fatty acid profiles in faecal samples analysed by gas-liquid chromatography on a scale from 0 to 100 between samples from atopics and non-atopics at 3 weeks and 3 months.

There were no statistically significant differences in gut microflora between atopics and non-atopics at the age of 3 months. The respective bacterial cellular fatty acid spectra were comparable (FIG. 3). Nor did results of bacterial cultivation differ between the groups, although non-atopics tended to have yeasts in their stools more frequently than atopics (Table 4) (p=0.07).

TABLE 3

Dietary characteristics and use of antibiotics in infants at 3 weeks and 3 months

|  | Atopics[a] (n = 22) | Non-atopics[a] (n = 54) | x²-test |
|---|---|---|---|
| 3 weeks: | | | |
| exclusively breastfed | 16/22 (73%) | 37/54 (68%) | 0.31 |
| partially breastfed | 6/22 (27%) | 15/54 (28%) | 0.96 |
| totally bottlefed | 0/22 | 2/54 (4%) | 0.36 |
| antibiotics[b] | 0/22 | 3/54 (6%) | 0.26 |
| 3 months: | | | |
| exclusively breastfed | 11/22 (50%) | 29/54 (54%) | 0.77 |
| partially breastfed | 6/22 (27%) | 14/54 (26%) | 0.90 |
| totally bottlefed | 5/22 (23%) | 11/54 (20%) | 0.82 |
| antibiotics[c] | 0/22 | 9/54 (17%) | 0.04 |

[a] Infants with at least one positive reaction in skin prick testing were considered atopic, those without non-atopic.

[b] and [c] represent the number of infants having received systemic antibiotics (orally or intravenously) by the ages of 3 weeks and 3 months, respectively

TABLE 4

Cultured faecal microflora in infants at 3 weeks and 3 months

|  | Yeasts and fungi[a] | Gram-neg rods[a] | Anaerobics[a] | Clostridium difficile[a] | Lacto- | Entero-bacilli[a] |
|---|---|---|---|---|---|---|
| 3 weeks: | | | | | | |
| Atopics[b] | 0/20 | 15/20 | 18/20 | 0/20 | 16/20 | 18/20 |
| Non-atopics[b] | 45/51 | 2/51 | 39/51 | 45/51 | 2/51 | 41/51 |
| $\chi^2$-test | 0.37 | 0.90 | 0.83 | 0.37 | 0.97 | 0.83 |
| 3 months: | | | | | | |
| Atopics[b] | 0/20 | 20/20 | 18/20 | 1/20 | 18/20 | 20/20 |
| Non-atopics[b] | 47/49 | 7/49 | 45/49 | 40/49 | 6/49 | 44/49 |
| $\chi^2$-test | 0.07 | 0.19 | 0.39 | 0.37 | 0.98 | 0.36 |

[a] Numbers in columns represent the number of infants having the bacterium/bacteria in faecal sample analysed by bacterial cultivation
[b] Infants with at least one positive reaction in skin prick testing were considered atopic, those without non-atopic.

TABLE 5

Bacterial counts in faecal samples analysed by fluorescence in situ hybridisation at the age of 3 weeks

|  | Atopics[a] | Non-atopics[a] | Unpaired t-test[c] |
|---|---|---|---|
| Clostridia[b] | 9.3 (3.8 to 22.9) × $10^7$ | 3.3 (1.8 to 6.1) × $10^7$ | 0.04 |
| Bifidobacteria[b] | 1.8 (0.4 to 7.6) × $10^9$ | 6.1 (2.5 to 14.6) × $10^9$ | 0.11 |
| Lactobacilli/enterococci[b] | 2.4 (1.1 to 5.2) × $10^8$ | 3.4 (1.5 to 7.6) × $10^8$ | 0.53 |
| Bacteroides[b] | 1.1 (0.3 to 4.4) × $10^8$ | 0.5 (0.2 to 1.4) × $10^8$ | 0.30 |
| Total cell count[b] | 8.9 (4.0 to 19.4) × $10^9$ | 9.6 (5.3 to 17.3) × $10^9$ | 0.87 |

[a] Infants with at least one positive reaction in skin prick testing were considered atopic, those without non-atopic.
[b] represents the geometric mean (95% CI) of faecal number of bacteria/g.
[c] Unpaired t-test was applied after logarithmic transformation of bacterial counts.

REFERENCES

Eerola E, Lehtonen O P. Optimal data processing procedure for automatic bacterial identification by gas-liquid chromatography of cellular fatty acids. J. Clin. Microbiol. 1988; 26:1745–1753.

Hanifin J M. Atopic dermatitis in infants and children. Pediatr. Clin. North Am. 1991; 38:763–789.

Isolauri E, Suomalainen H, Kaila M, et al. Local immune response in patients with cow milk allergy: follow-up with patients retaining allergy or becoming tolerant. J. Pediatr. 1992; 120:9–15.

Isolauri E, Arvola T, Sütas Y, Moilanen E., Salminen S. Probiotios in the management of atopic eczema. Clin. Exp. Allergy 2000; 30:1605–1610.

Isolauri E, Majamaa H, Arvola T. et al. *Lactobacillus casei* strain GG reverses increased intestinal permeability induced by cow milk in suckling rats. Gastroenterology 1993; 105: 1643–1650.

Kalliomäki M, Ouwehand A, Arvilommi H, Kero P, Isolauri E. Transforming growth factor-beta in breast milk: a potential regulator of atopic disease at an early age. J. Allergy Clin. Immunol. 1999; 104:1251–1257.

Langendijk P S, Schut F, Jansen G J, Raangs G C, Kamphuis G R, Wilkinson M H, et al. Quantitative fluorescence in situ hybridization of *Bifidobacterium* spp. with genus-specific 16S rRNA-targeted probes and its application in fecal samples. Appl. Environ. Microbiol. 1995; 61:3069–75.

Majamaa H, Isolauri E. Evaluation of the gut mucosal barrier: evidence for increased antigen transfer in children with atopic eczema. J. Allergy Clin. Immunol. 1996; 97: 985–990.

Majamaa H, Isolauri E. Probiotics: a novel approach in the management of food allergy. J. Allergy Clin. Immunol. 1997; 99:179–185.

Pessi T, Sütas Y, Marttinen A, Isolauri E. Down-regulation of anti-CD3 antibody-induced IL-4 production by bovine caseins hydrolysed with *Lactobacillus* GG-derived enzymes. J. Nutr. 1998; 128: 2313–2318.

Sanfilippo L, Li C K, Seth R, Balwin T J, Menozzi M G, Mahida Y R. *Bacteroides fragilis* enterotoxin induces the expression of IL-8 and transforming growth factor-beta (TGF-beta) by human colonic epithelial cells. Clin. Exp. Immunol. 2000; 119:456–463.

What is claimed is:

1. A method for prevention of atopic diseases selected from the group consisting of atopic eczema, allergic rhinitis and asthma in an infant at high risk of said atopic diseases, comprising administering to a pregnant woman a daily dose of live probiotic bacteria in an amount of about $1 \times 10^8$ to about $1 \times 10^{10}$ colony forming units of the probiotic bacteria for at least two weeks before infant delivery, and after infant delivery, administering directly to the newborn infant of said pregnant woman a daily dose of live probiotic bacteria in an amount of about $1 \times 10^8$ to about $1 \times 10^{10}$ colony forming units of the probiotic bacteria for at least 2 months;

wherein said probiotic bacteria are selected from the group consisting of *Lactobacillus casei* spp. *rhamnosus* ATCC 53103 and *Bifidobacterium lactis* Bb-12.

2. The method according to claim 1, wherein the administering of said live probiotic bacteria to said pregnant woman and to said newborn infant results in promoting early bifidogenic gut microflora.

* * * * *

SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence -continued

```
<220> FEATURE:
<223> OTHER INFORMATION: Description of artificial sequence:
      oligonucleotide probe Bac303

<400> SEQUENCE: 1
ccaatgtggg ggacctt                                                  17

<210> SEQ ID NO 2
<211> LENGTH: 18
<212> TYPE: DNA
<213> ORGANISM: Artificial Sequence
<220> FEATURE:
<223> OTHER INFORMATION: Description of artificial sequence:
      oligonucleotide probe Bif164

<400> SEQUENCE: 2
catccggcat taccaccc                                                 18

<210> SEQ ID NO 3
<211> LENGTH: 23
<212> TYPE: DNA
<213> ORGANISM: Artificial Sequence
<220> FEATURE:
<223> OTHER INFORMATION: Description of artificial sequence:
      oligonucleotide probe His150

<400> SEQUENCE: 3
ttatgcggta ttaatctycc ttt                                           23

<210> SEQ ID NO 4
<211> LENGTH: 20
<212> TYPE: DNA
<213> ORGANISM: Artificial Sequence
<220> FEATURE:
<223> OTHER INFORMATION: Description of artificial sequence:
      oligonucleotide probe Lab158

<400> SEQUENCE: 4
ggtattagca yctgtttcca                                               20
```